United States Patent [19]

Lednicer et al.

[11] 4,008,208

[45] Feb. 15, 1977

[54] COMPOSITIONS HAVING INHIBITED ABILITY TO PROMOTE PLATELET AGGREGATION OR FIBRIN CLOT FORMATION

[75] Inventors: Daniel Lednicer, Portage; Edward E. Nishizawa, Schoolcraft, both of Mich.

[73] Assignee: The Upjohn Company, Kalamazoo, Mich.

[22] Filed: Mar. 17, 1975

[21] Appl. No.: 559,333

Related U.S. Application Data

[62] Division of Ser. No. 258,016, May 30, 1972, Pat. No. 3,888,833.

[52] U.S. Cl. .................... 260/79.3 R; 424/78; 526/22; 526/30
[51] Int. Cl.² .................... C08F 8/36; C08F 28/02
[58] Field of Search ..... 260/79.3 R, 93.7, 94.9 GD, 260/94.9 GB; 526/22, 30

[56] References Cited

UNITED STATES PATENTS

| | | | |
|---|---|---|---|
| 3,044,987 | 7/1962 | Schaefgen et al. | 260/79.3 R |
| 3,374,210 | 3/1968 | Muller et al. | 260/79.3 R |
| 3,471,431 | 10/1969 | Mann et al. | 260/79.3 R |
| 3,801,531 | 4/1974 | Berejka et al. | 260/79.3 R |
| 3,857,823 | 12/1974 | Ackermann | 260/79.3 R |

*Primary Examiner*—Ronald W. Griffin
*Attorney, Agent, or Firm*—Martin B. Barancik; Roman Saliwanchik

[57] ABSTRACT

A composition which comprises a substance which is a substituted aromatic and which inhibits the thrombotic or clotting activity of a material, chemically bonded through an —N=N— grouping to a second aromatic which is chemically bonded at a sulfonyl grouping through a nitrogen containing chemical bond to a material which is susceptible to interaction with a nitrene.

9 Claims, No Drawings

COMPOSITIONS HAVING INHIBITED ABILITY TO PROMOTE PLATELET AGGREGATION OR FIBRIN CLOT FORMATION

CROSS REFERENCE TO RELATED APPLICATIONS

This application is a divisional of co-pending application Ser. No. 258,016, filed May 30, 1972 and now issued as U.S. Pat. No. 3,888,833.

BACKGROUND OF THE INVENTION

Technological advances in the last few decades have brought the mammalian body in intimate contact with a variety of devices incorporating foreign materials which were not present in the evolution of their systems. Although many of these devices function as designed, a substantial number of them suffer from serious drawbacks. This appears to be particularly true when a device prepared from a foreign material is in contact with the blood of a mammal. All presently available materials which are in contact with the blood for significant periods of time induce deposition of blood cells and fibrin. This problem has hampered the practical development of artificial organs, extracorporeal shunts, renal dialysis systems, catheters, heart-lung machines and the like. Solution of the problem is also important for in vitro systems such as blood collection and storage containers, for example.

Interaction of blood with the surface of a foreign material can result in two related but distinct processes. The first is a formation of a platelet thrombus which may lead to a second process, namely, coagulation, particularly in areas of slow blood flow. However, coagulation can occur in the absence of platelet interaction, particularly in in vitro systems.

The platelet thrombosis process is initiated by the adherence of blood platelets to the foreign surface with subsequent platelet-platelet interaction or aggregation leading to formation of a thrombus composed almost entirely of platelets. In areas of rapid blood flow, such as the cage of an artificial heart valve or in arterial grafts, the primary difficulty is platelet thrombosis and thromboembolism. Aggregated platelets release a factor which may stimulate a second process, blood coagulation, leading to formation of a fibrin blood clot. Clot formation is of major importance in areas of slow blood flow such as around the sewing ring of a valve or in venous circulation. Although platelet thrombi do not always result in clot formation, they can produce deleterious effects themselves. Since there is not a generic description covering both of these processes, a substance which inhibits platelet aggregation will hereinafter be referred to as "antithrombotic" and a substance which inhibits fibrin clot formation will hereinafter be referred to as "anticlotting".

Previously, researchers have attacked the problem of deposition of blood cells and fibrin on the surfaces of materials primarily by attempting to inhibit clot formation. The most common approach has been to coat the surface or impregnate the material with an anticoagulant, primarily heparin. Because there is no known method of directly binding heparin to materials, the heparin is bound to an intermediate chemical which is also bound to the particular material.

The binding of the intermediate to the material was done initially through adsorption. Since this surface gradually wore off the material, an ionic type of intermediate became employed more frequently. The lifetime of this coating was generally longer but it gradually wore off, as well. Recently, the intermediate compound has been covalently bound to the material. However, this covalent bonding is dependent upon a reactive group such as gamma propylamine in or interspersed within the material, or on radiation grafting.

BRIEF SUMMARY OF THE INVENTION

We have now found a new means of covalently bonding antithrombotic or anticlotting compounds to a material. This bonding is brought about by the chemical attachment of the antithrombotic or anticlotting substance to an aromatic sulfonyl nitrene which is chemically bonded to the material, apparently through means of a sulfonamide-type bond. Any material which is susceptible to this type of interaction can have its ability to promote platelet aggregation or fibrin clot formation inhibited.

Therefore, it is in accordance with this invention that we have discovered a method for binding antithrombotic or anticlotting substances to a susceptible material involving the use of an aromatic sulfonyl nitrene.

A further aspect of this invention involves the composition of the antithrombotic or anticlotting substance, the aromatic sulfonyl nitrene, and the material; and the method of inhibiting platelet aggregation or fibrin clot formation with these compositions.

A still further aspect of the invention is the aromatic sulfonyl nitrene antithrombotic or anticlotting substance intermediate.

The formation of intermediate compositions of the aromatic sulfonyl nitrene and the material is another aspect of this invention.

DETAILED DESCRIPTION OF THE INVENTION

The materials to which antithrombotic or anticlotting substances can be indirectly bound are materials which are susceptible to reaction with an aromatic sulfonyl nitrene. Generally these materials are polymers, either synthetic or natural, with a plurality of carbon-hydrogen bonds. The preferable materials include polyethylene, polypropylene, natural or synthetic rubbers, a polyester such as Dacron, nylons, polyurethanes, and the like.

The actual compound which is bound to the surface of the material is the aromatic sulfonyl nitrene. The reaction route appears to be the insertion of the nitrene into a carbon and hydrogen bond of the polymer upon irradiation of an azide, thus forming a sulfonamide. This is illustrated below with a para nitrobenzenesulfonamide.

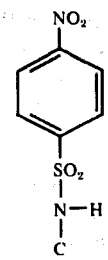

Figure 1

The aromatic sulfonyl nitrene which can be bound to the surface of the material is selected from the group of aromatic sulfonyl nitrenes consisting of

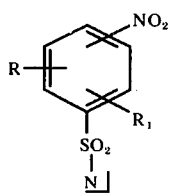

Figure II wherein R and $R_1$ can be the same or different and are selected from the group consisting of hydrogen, halogen, and normal or isomerized alkyl from one to four carbon atoms, inclusive, and

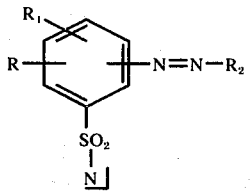

Figure III where R and $R_1$ are defined as in FIG. 11 above and $R_2$ is a substance which inhibits the thrombotic or clotting activity of the material and is that portion of a substituted aromatic which couples with a diazonium salt. Halogen is fluorine, chlorine, bromine, and iodine. Alkyl is methyl, ethyl, propyl, butyl, and isomers thereof.

Aromatic sulfonyl nitrenes of FIG. 11 are made from sulfonylchlorides by conversion of the sulfonyl chloride to the corresponding sulfonylazide. The azide is converted to the corresponding nitrene by irradiation. Illustrative sulfonylchloride starting materials for the nitrenes of FIG. 11 are the following compounds:

2-bromo-5-nitrobenzenesulfonylchloride
2-chloro-4-nitrobenzenesulfonylchloride
2-chloro-5-nitrobenzenesulfonylchloride
4-chloro-2-nitrobenzenesulfonylchloride
4-chloro-3-nitrobenzenesulfonylchloride
4-fluoro-3-nitrobenzenesulfonylchloride
4-propyl-2-nitrobenzenesulfonylchloride
4-tertbutyl-2-nitrobenzenesulfonylchloride
4-propyl-2-chloro-5-nitrobenzenesulfonylchloride
4-nitro-o-toluenesulfonylchloride
5-nitro-o-toluenesulfonylchloride
3-nitro-o-toluenesulfonylchloride
5-chloro-3-nitro-o-toluenesulfonylchloride
2,4-dichloro-5-nitrobenzenesulfonylchloride
4-propyl-6-methyl-2-nitrobenzenesulfonylchloride Illustrative compounds of FIG. 111 are the aromatic sulfonyl nitrenes of FIG. 11 with the $R_2$ compound being that portion of the following illustrative substituted aromatics which couple with a diazonium salt:

8-amino-1-naphthol-5,7-disulfonic acid
1-amino-2-naphthol-4-sulfonic acid
4,5-dihydroxynaphthalene-2,7-disulfonic acid
2,3-dihydroxynaphthalene-6-sulfonic acid
7-amino-1-naphthol-3,6-disulfonic acid
8-amino-1-naphthol-3,6-disulfonic acid
1-naphthol-3,6-disulfonic acid
2-naphthol-3,6-disulfonic acid
1-naphthol-4-sulfonic acid
2-naphthol-7-sulfonic acid
α-methyl-2-fluoro-2'-hydroxy-4-biphenylacetic acid
α-methyl-2-fluoro-4'-hydroxy-4-biphenylacetic acid The preferred substituted aromatic is 8-amino-1-naphthol-5,7-disulfonic acid.

The preferred R and $R_1$ substituents of FIG. 11 and FIG. 111 compounds include compounds where R is hydrogen, chloride, bromide, and alkyl from one to three carbon atoms, inclusive.

The most preferred are those compounds where R and $R_1$ are hydrogen and the nitro group is meta or para.

The compounds and compositions of the invention can be prepared by methods known in the art. The synthesis of FIG. 11 and FIG. 111 compounds, aromatic sulfonylnitrene-material intermediate compositions and final compositions of the material-aromatic sulfonyl nitrene-antithrombotic or anticlotting substance will be illustrated employing the meta-nitrobenzenesulfonylnitrene compound. It is to be understood that this compound can be substituted with R and $R_1$ as defined above.

Nitrobenzene is chlorosulfonated at the meta position when contacted with chlorosulfonic acid to form meta-nitrobenzenechlorosulfonic acid. The chlorosulfonic acid is then converted to the sulfonylazide by reacting with sodium azide in a solution of aqueous methanol. The compounds of FIG. 11 and the material-nitroaromatic sulfonyl nitrene intermediate compositions are prepared by irradiating the azide when in contact with a material susceptible to attack by a nitrene. If proper adherence between the material and the aromatic sulfonylazide is difficult to maintain prior to and during the course of irradiation, as with polyethylene, for example, an inert carrier such as Fluorolube S-30, a perfluorinated mineral oil obtained from Hooker Chemical Company, can be employed in order to maintain the appropriate contact.

The types of radiation which can be employed to convert the azide to the nitrene include ultraviolet, ultrasound, and X-ray. Generally, any radiation which promotes removal of free nitrogen from an azide can be employed. The irradiation time should be of sufficient length to promote the removal of nitrogen from the azide but of insufficient length to cause alteration of the material's desirable characteristics. This irradiation time may vary from an hour or more to a mere "flash" photolysis.

After formation of the aromatic sulfonylnitrene material composition, the nitro grouping on the aromatic nucleus is conveniently reduced to an amino group by a reduction involving metals, for example, stannous chloride in hydrochloric acid. Sodium thiosulfate in sodium hydroxide is effective as well.

The amino grouping is then diazotized. Nitrous acid prepared in situ by the reaction of sodium nitrite and hydrochloric acid is a suitable reagent for the conversion. Once the diazonium salt is formed, it can be coupled with a substance which possesses antithrombotic or anticlotting activity such as aforementioned. Standard diazonium salt coupling reaction conditions can be employed. The thrombogenic or clotting activity of the material is inhibited by the coating affixed to the material by way of the aromatic sulfonyl nitrene molecule.

If compounds of FIG. 111 are desired, a nitroaromatic is reduced to an amino by way of the methods previously stated. The amino group is then diazotized with nitrous acid and the resulting diazonium salt coupled with an antithrombotic or anticlotting substance as aforementioned. This product is then reacted in turn with chlorosulfonic acid and sodium azide. This intermediate compound is then contacted with a material which is susceptible to interaction with a sulfonyl nitrene and then irradiated. The thrombogenic or clotting activity of the material is inhibited by the coating affixed to the material by way of the aromatic sulfonylnitrene.

The actual bonding of the aromatic sulfonyl nitrene to the material is difficult to identify since conventional means of crystallization and analysis are not applicable to the system of this invention. Because of the well-known ability of a nitrene to insert into a carbon-hydrogen bond, see D. Breslow in "Nitrenes", Lwowski, Ed. Interscience, N.Y., 1970., and the absence of any reactive groups in polymers such as polyethylene and polypropylene, the most reasonable assignment for the reaction product is that of a sulfonamide.

The following examples are not intended to limit but only to illustrate the invention:

EXAMPLE 1

A solution of 0.6 gram each of m- and p-nitrobenzenesulfonylazide, the combination of isomers selected so as to reduce crystallinity, and 1.2 milliliters of Fluorolube S-30 oil in 12 milliliters of acetone is prepared. A fifteen $cm^2$ sheet of polyethylene, showing no absorption in the ultraviolet down to 230 nm., is sprayed with one-half of this solution. The sheet is covered with a Vycor plate, an ultraviolet transparent quartz glass, and irradiated for one hour under a low pressure mercury lamp. The sheet is then rinsed with acetone, sprayed with the remaining solution and irradiated with the low pressure mercury lamp for another hour.

The sheet is rinsed with acetone and stirred at room temperature with 10.0 gram of stannous chloride in 100 milliliters concentrated HCl for 4 hours. The sheet is then removed, rinsed with water, stirred for fifteen minutes with 1N sodium hydroxide and rinsed again with water.

The sheet is then exposed for two minutes to an ice cold solution of nitrous acid prepared from fifty milliliters of 2.5N HCl and 5 grams of sodium nitrite in twenty milliliters of water. Following a brief rinse with ice water, the sheet is immersed for two minutes in a 10% aqueous solution of the monopotassium salt of 8-amino-1-naphthol-5,7-disulfonic acid. This couples the dye to a diazonium salt. The sheet is then washed with acetone and dried and subjected to ultraviolet analysis once more. This sample shows an ultraviolet absorption bond at 250 nm which demonstrates the attachment of a chromaphore..

EXAMPLE 2

A suspension of 3.8 grams of m-toluidine in four milliliters concentrated HCl and 20 milliliters of water is cooled in an ice-methanol bath. 2.3 grams of sodium nitrite in a minimum amount of water is added. After five minutes, this solution is added to 10 grams of 8-amino-1-naphthol-5,7-disulfonic acid in fifty milliliters of water. The fine precipitate is collected on a filter and vacuum dried to give a dark red powder. Infra red and ultraviolet analysis show this powder to be the coupling product.

1.73 grams of the above prepared powder is added to ten milliliters of chlorosulfonic acid. After 6 hours of vigorous stirring, the mixture is poured into a small amount of ice water. The precipitated chlorosulfonate, as identified by I. R., is collected on a filter and vacuum dried.

Two grams of sodium azide in ten milliliters of $H_2O$ is added to a solution of the sulfonyl chloride. Small aliquots are removed and worked up to monitor for appearance of sulfonyl azide. ($IR_{max}$ 2250 $cm^{-1}$). When the reaction is complete the cosolvent is removed under vacuum and the residue suspended in a small amount of ice water. The residual reddish solid is then collected on a filter.

The powder is coated on the polyethylene and irradiated in the same manner as Example 1, the nitrene being formed and apparently inserting into a carbon-hydrogen bond of the material.

EXAMPLE 3

The following procedures for testing the antithrombotic activity of a coated material is employed in later examples.

A Y-tube extracorporeal shunt is placed between the carotid artery and the jugular vein of a rabbit. When a treated polymer, which can be shaped into a thin flexible sheet, is under study, a small piece of the treated polymer is placed in one arm of the Y-tube. The other arm is similarly lined with a portion of the non-treated polymer for use as a control. When a treated polymer which is relatively inflexible is studied, a straight section of the treated polymer is connected directly into the carotid jugular by-pass. An untreated control section is placed in tandem.

The animal is given 100 $\mu$/kg. of heparin and the shunt is allowed to flow for one hour. The Y-tube is disconnected, rinsed gently in Tyrodes' solution followed by distilled water and ethanol. The materials are then stained with Luxol Blue, a dye, visually observed and photographed. The platelet deposits on the control and treated polymer are then compared.

EXAMPLE 4

The following procedure for testing the anticlotting activity of a coated material is employed.

A polyethylene or polypropylene test tube is coated with the desired anticlotting substance using the methods employed in this disclosure. Whole blood is collected into these tubes and allowed to clot and assayed by the tilting tube method. Platelet involvement in this reaction can be minimized by adding an inhibitor of platelet aggregation which does not interfere with blood coagulation. A control tube without a coating and a control tube with a coating of the nitro or amino aromatic sulfonyl nitrene are tested at the same time.

Differences in clotting time from the control tube and the treated tube are measured.

EXAMPLE 5

Following the procedure of Example 1, polypropylene tubing was made nonthrombotic with 8-amino-1-naphthol-5,7-disulfonic acid. The treated tube was then tested for nonthrombogenicity in accordance with the method of Example 3. Virtually no deposit of platelets was observed on the treated polypropylene but substantial deposits were on the control.

EXAMPLE 6

Following the procedure of Example 1, polyethylene, Dacron, and latex were made nonthrombogenic with 8-amino-1-naphthol-5,7-disulfonic acid. The treated polyethylene surface was almost devoid of platelets.

7

The treated latex showed substantially less deposit than the untreated control. Since the deposits on the treated tubing were primarily across the lateral portion of the tubing, the deposits may be due to cracks produced by the inversion of the tubing for treatment.

With regard to the Dacron employed, it also appears to have less platelet deposits upon it than upon the control. However, a significant portion of the platelet deposits on the treated Dacron may be due to the Silastic backing on the Dacron, since previous work has shown that the treatment of Silastic with the coating material causes the Silastic to deteriorate, thereby causing greater platelet deposition.

EXAMPLE 7

In accordance with the method of Example 1, a polyethylene sheet is contacted with the m-nitro aromatic sulfonyl azide and irradiated. The resulting treated sheet is tested for nonthrombogenecity in accordance with the method of Example 3. Upon inspection, substantially the same number of platelets are on both the treated and the control sheets. Consequently, a nonthrombogenic effect has not been imparted to the treated polyethylene by the nitro aromatic sulfonyl nitrene.

In like manner, p-amino aromatic sulfonyl azide is contacted with a polyethylene sheet and irradiated. The resulting treated sheet is tested for nonthrombogenecity as in Example 3. A nonthrombogenic effect is not imparted to the treated polyethylene by the amino aromatic sulfonyl nitrene.

These results support the interpretation that it is the antithrombotic substance coupled to the diazonium salt which inhibits the thrombotic effects of the polymeric material.

The small quantity of heparin administered to the subject rabbit does not appear to alter the results of the experiments. Heparin interferes with fibrin formation and does not inhibit the deposition of platelets. Furthermore, since the same animal is used for evaluating both control and treated materials, any effect of heparin appears to be nullified.

We claim:

1. A composition which comprises a sulfonyl aromatic diazonium salt chemically bonded at the sulfonyl grouping through a nitrogen-containing bond to a material which is susceptible to interaction with a nitrene which induces deposition of blood cells and fibrin when in contact with mammalian blood.

2. A composition which comprises

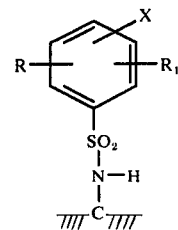

wherein X is nitro or amino, R and $R_1$ are the same or different and are each selected from the group consisting of hydrogen, halogen, and alkyl of one to four carbon atoms, inclusive; and ─⫶⫶⫶─ C ─⫶⫶⫶─ is a material which is susceptible to interaction with an aromatic nitrene which induces deposition of blood cells and fibrin when in contact with mammalian blood.

3. A composition in accordance with claim 2 wherein X is nitro.

4. A composition in accordance with claim 2 wherein X is amino.

5. A composition which comprises a substituted aromatic compound that inhibits the thrombotic or clotting activity of a material susceptible to interaction with a sulfonylnitrene, said material being one which induces deposition of blood cells and fibrin when in contact with mammalian blood, said substituted aromatic compound is chemically bonded to a phenyl, monosubstituted phenyl, or disubstituted phenyl, which is chemically bonded to a sulfonyl group through a nitrogen-containing chemical bond to said material.

6. A composition in accordance with claim 5 wherein the material is a synthetic or natural polymer with a plurality of carbon-hydrogen bonds.

7. A composition in accordance with claim 6 wherein the nitrogen-containing bond to the material is a covalent bond between the nitrogen and a carbon atom of the material.

8. A composition in accordance with claim 7 wherein the phenyl, monosubstituted phenyl or disubstituted phenyl is

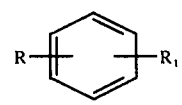

wherein R and $R_1$ are the same or different and are selected from the group consisting of hydrogen, halogen, and alkyl of one to four carbon atoms, inclusive.

9. A composition in accordance with claim 6 wherein the material is polyethylene or polypropylene.

* * * * *